United States Patent [19]

Mori

[11] Patent Number: 4,958,423
[45] Date of Patent: Sep. 25, 1990

[54] WATER-SUPPLYING CORD AND A TOOL FOR INSERTING A HOSE IN IT

[75] Inventor: Hidenobu Mori, Tokyo, Japan

[73] Assignee: OSADA Electric Co., Ltd., Tokyo, Japan

[21] Appl. No.: 398,198

[22] Filed: Aug. 24, 1989

Related U.S. Application Data

[62] Division of Ser. No. 192,811, May 11, 1988.

[30] Foreign Application Priority Data

Oct. 2, 1987 [JP] Japan ................. 62-152110
Dec. 31, 1987 [JP] Japan ................. 62-200773

[51] Int. Cl.$^5$ .......................................... B23P 19/02
[52] U.S. Cl. .................................................. 29/235
[58] Field of Search ................. 29/234, 235, 237, 280

[56] References Cited

U.S. PATENT DOCUMENTS

| 4,341,002 | 7/1982 | Diba | 29/280 |
| 4,581,805 | 4/1986 | Wrobel et al. | 29/235 |
| 4,593,442 | 6/1986 | Wright et al. | 29/235 |
| 4,716,641 | 1/1988 | Shrimpton | 29/235 |

Primary Examiner—Robert C. Watson
Attorney, Agent, or Firm—Jordan and Hamburg

[57] ABSTRACT

An electricity-supplying and water-supplying cord for use in dental surgery is made of a bendable, resilient member and has at least one hole for inserting electricity-supplying wires therethrough and one hole for inserting a water-supplying hose therein. The cord is provided with a straight rift along the axis of the hole for use in inserting the water-supplying hose. Further, a hose-inserting tool provides for inserting the resilient water-suppling hose into the hole which is formed in the abovementioned electricity-supplying and water-supplying cord.

5 Claims, 3 Drawing Sheets

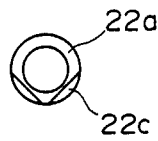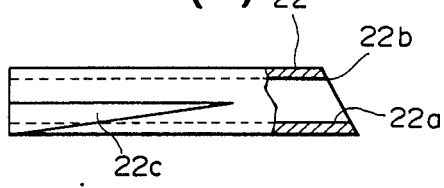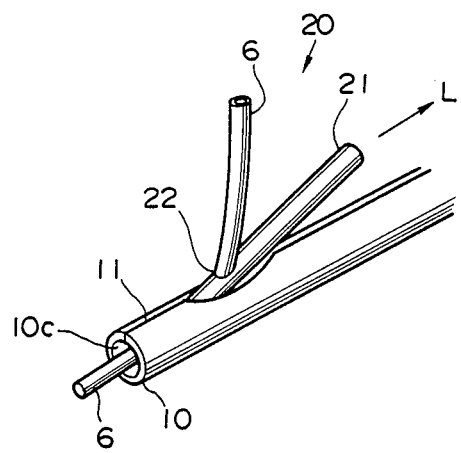

WATER-SUPPLYING CORD AND A TOOL FOR INSERTING A HOSE IN IT

This is a division, of application Ser. No. 192,811, filed May 11, 1988.

BACKGROUND OF THE INVENTION

The present invention relates to an electricity-supplying and water-supplying cord, in particular, an electricity-supplying and water-supplying cord which can accommodate in the same cord a hose for supplying a physiological solution of salt (salt water) and wires for supplying electric power to a micro-motor for administering medical treatment by supplying the salt solution and by driving the micro-motor at the same time, as an example, for use in the field of dental surgery.

Further, the present invention relates to a hose-inserting tool for inserting a resilient hose into a resilient cord, as mentioned above, having a hole with a rift formed along its axis.

With respect to dental surgical treatment, a dentist performs dental surgical treatment on a patient by using a dental surgical treatment unit. The above-mentioned dental surgical treatment unit has a work table which is equipped with an instrument used for performing dental surgical treatment and a pumping means for forcibly sending a physiological solution of salt to the patient's mouth which is used for cleaning the spot just treated.

The instrument used for performing the dental surgical treatment is constructed with a controller, a micro-motor which is controlled by the controller and thereby rotatably drives a cutting bar. The pumping means for forcibly sending out a physiological solution of salt comprises a tank for accommodating a cleaning liquid such as the afore-mentioned solution, a water-supplying hose for forcibly sending out pressurized air, controlled by the above-mentioned controller, to the tank and for guiding the pressurized air into the instrument in order to eject the same therefrom.

Conventionally, the power source cord for rotatably driving the micro-motor and the water-supplying hose for guiding the cleaning liquid are arranged individually. Such an arrangement is more complicated, inconvenient to use and unattractive. For such reasons, the present applicant has proposed an electricity-supplying and water-supplying cord capable of combining the two into one unit. Concerning this cord, the power source cord and the water-supplying hose are respectively inserted into each of the insertion holes formed in a resilient, integrally-molded member and provided with a hole for accommodating therein the water-supplying hose with a rift along the axis of the hole for the purpose of putting in another water-supplying hose after taking out the old used water-supplying hose. As mentioned before, the water-supplying hose is used for sending out a physiological solution of salt and consequently crystals of salt tend to build up inside the hose and cause clogging. For this reason, it is necessary from time to time to take out the water-supplying hose through the rift portion and to clean it or to make it possible to exchange the old one for a new one.

SUMMARY OF THE INVENTION

It is an object of the present invention to provide an electricity-supplying and water-supplying cord which can accommodate in the same cord a hose for supplying a physiological solution of salt (salt water) and wires for supplying electric power to a micro-motor for administering medical treatment by supplying the salt solution and by driving the micro-motor at the same time, as an example, for use in the field of dental surgery.

It is another object of the present invention to provide an electricity-supplying and water-supplying cord capable of easily removing an older used hose and for replacing the afore-mentioned water-supplying hose simply and easily.

It is another object of the present invention to provide an electricity-supplying and water-supplying cord having a hole for inserting a water-supplying hose therein and also provided with a straight rift along the axis of said hole for inserting said water-supplying hose.

It is another object of the present invention to provide a hose-inserting tool for inserting a resilient water-supplying hose into a hole which is formed in the above-mentioned electricity-supplying and water-supplying cord and which has a rift along the water-supplying hole's axis.

It is another object of the present invention to provide a hose-inserting tool capable of inserting simply a water-supplying hose into an insertion hole formed in an electricity-supplying and water-supplying cord.

BRIEF DESCRIPTION OF THE DRAWINGS

FIG. 3 is a construction view showing a hose-inserting tool according to the present invention, wherein FIG. 3b is a plane view thereof as seen from the direction shown from below in FIG. 3a, and FIG. 3c is a cross-sectional view thereof taken along the section line X—X of FIG. 3a;

FIGS. 4a, 4b and 4c are detailed views showing the hose guide in more detail 12 as shown in FIG. 3; and FIG. 5 is a perspective view showing a method for using the hose-inserting tool according to the present invention.

DESCRIPTION OF THE PREFERRED EMBODIMENTS

Figure 1:
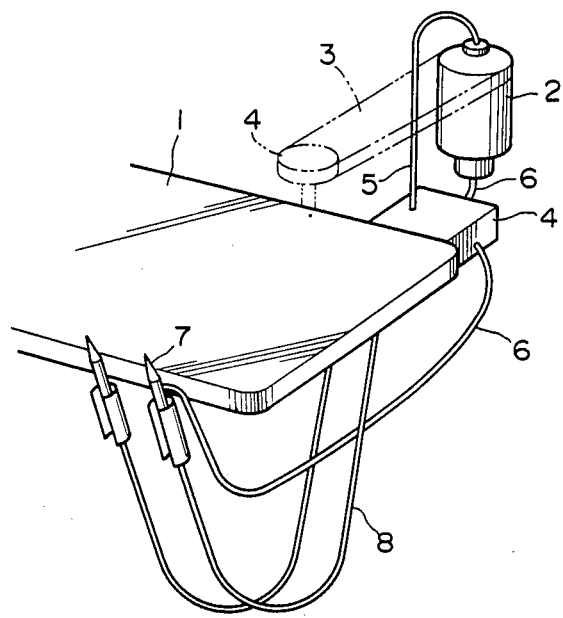
FIG. 1 is a perspective construction view for explaining an embodiment of the conventional electricity-supplying and water-supplying unit.

FIG. 1 is a perspective construction view for showing the main part of a conventional dental surgery treatment unit. In FIG. 1, the reference numeral 1 represents a work table, 2 a tank containing a physiological solution of salt or refined distilled water, 3 an arm for mounting the tank 2 thereon, 4 a controller box, 5 a hose for supplying pressurized air, 6 a supply hose for supplying a physiological solution of salt or refined distilled water, 7 an instrument for performing dental surgical treatment such as a micro-motor, a scaler or the like driven by electric power, and 8 a cord for supplying electric power to the afore-mentioned instrument. The above-mentioned unit comprises the tank for accommodating a physiological solution of salt or refined distilled water. When the dental surgical operation is performed, a physiological solution of salt or refined distilled water can be used instead of service water as the occasion demands and thereby surgery can be facilitated.

However, with respect to the above-mentioned conventional unit, the instrument 7 needed the cord 8 for supplying electric power and a water-supplying hose 6 for ejecting a physiological solution of salt from the tip of the instrument 7. And further, the cord 8 and the hose 6 were complicatedly arranged and were therefore very inconvenient to use and not attractive.

The above-mentioned electricity-supplying and water-supplying cord 10 comprises a resilient body made of resin material having holes 10a, 10b and a hole 10c both formed therein, electricity-supplying cords 8a, 8b inserted into the holes 10a, 10b and a water-supplying hose 6 inserted into the hole 10c. The hole 10c is provided with a rift 11 along its axis. The water-supplying hose 6 is inserted into the hole 10c through the rift 11 which is opened by hand. After inserting the hose 6 thereinto, it becomes tighter because of the cord's elasticity. However, usually the work of inserting the hose 6 into the hole 10c through the rift 11 is very troublesome and time-consuming.

Figure 2:
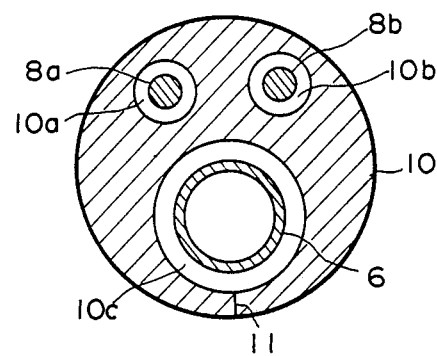
FIG. 2 is a cross-sectional construction view for explaining an embodiment of the electricity-supplying and water-supplying cord according to the present invention.

FIG. 2 is a cross-sectional construction view for explaining an embodiment of an electricity-supplying and water-supplying cord according to the present invention. In FIG. 2, the reference numeral 10 represents a cord made of a single bendable, resilient member, as for instance silicon or the like. Holes 10a and 10b are for inserting therethrough lead wires 8a and 8b for supplying electric power and another hole 10c for inserting therethrough a hose 6 for supplying a physiological solution of salt (salt water) are bored into the cord 10. And further, the cord 10 is provided with a straight rift 11 along the axis of the hole 10c.

The afore-mentioned electricity-supplying and water-supplying cord is, at the time of employing it, cut into several meters of length and employed for performing dental surgical treatment. The electricity-supplying cord and the water-supplying hose, etc. can be easily inserted into the main cord 10 from one of the end portions thereof. However, the afore-mentioned hose for supplying a physiological solution of salt sometimes gets clogged up or its interior becomes contaminated. Therefore, it is necessary to substitute a new one or to disinfect the old one from time to time. In the case of inserting the cords 8a, 8b and the hose 6 into the cord 10 from one of the end portions thereof, on all such occasions as mentioned before, it takes a lot of time to conduct the operation and it is very complicated.

The present invention was made for the purpose of eliminating such inconveniences. As shown in FIG. 2, the hole 10c for inserting therethrough the water-supplying hose 6 is provided with a straight rift 11 along the axis. When the water-supplying hose 6 is attached to and detached from the dental surgical treatment instrument, the rift 11 is utilized for taking out and putting in the hose 6. Although the cord 10 has two holes 10a, 10b for inserting therethrough the electricity-supplying cords 8a, 8b in the embodiment of FIG. 2, it is also true that the cord 10 has only one hole in the case of using an insulated, electricity-supplying cord.

As is apparent from the foregoing description, according to the present invention, it may be possible to accommodate the electricity-supplying cord and the water-supplying hose into a single cord of a simple, low-cost construction and to arrange the same at a suitable spot, and further to be able to remove and replace the afore-mentioned water-supplying hose simply and easily.

Figures 3A, 3C:
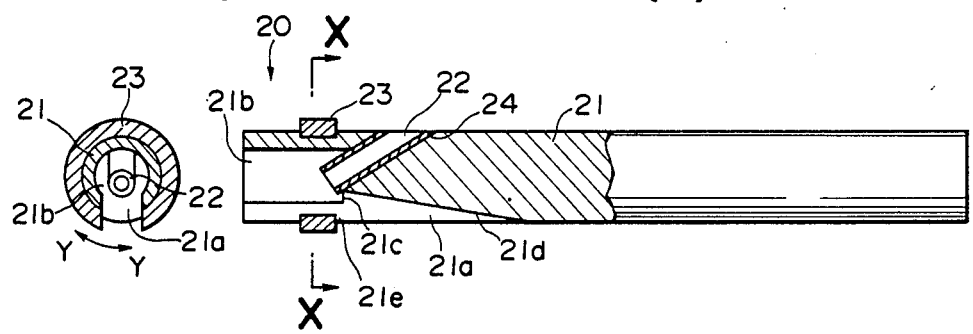
FIG. 3a is a side view thereof.
Figure 3B:
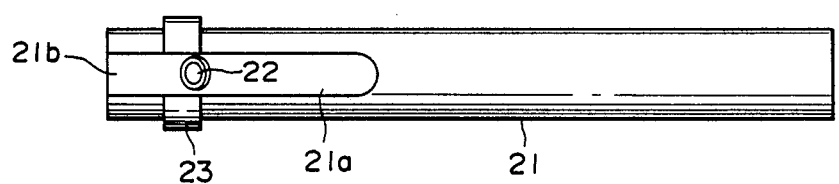

FIG. 3 shows an embodiment of a tool used for inserting the water-supplying hose according to the present invention. FIG. 3a is a side view partially showing a cross-section of the tool, FIG. 3b a plane view showing the tool as seen from the below of FIG. 3a, and FIG. 3c is a cross-sectional view taken along the section line X—X shown by the arrow in FIG. 3a.

In FIG. 3, the reference numeral 20 represents a tool assembly in itself. The tool in itself 20 is constructed of a bar-like body 21 consisting of a resin material. At one end thereof, an opening portion 21b is bored so as to open on the axis of the bar-like body. A part of the cylindrical portion formed by the tool itself 20 and the opening portion 21b thereof is removed in the direction of the axis of the cylindrical portion to forms a groove 21a having a tapered groove 21d tapered toward another end of the tool 20. The reference numeral 22 represents a hose guide. One end thereof is opened so as to be opposite to the bottom surface of the opening portion 21b of the tool 20, and another end thereof is tightly fixed to the hose-guiding hole 24 which is opened at the surface of the reverse side of the groove 21a. The hose guide 22 as mentioned above is made of a hard metal.

FIG. 4a~4c show the details of the afore-mentioned hose guide 22. In the case of tightly attaching a cylindrical body of the hose guide 22 having an insertion hole 22a to the tool itself 20, the surface portion of the tool 20 has a tapered surface 22b so as to be on the same surface level, while the opening portion 21b has a V-shaped tapered surface 22c such that the removed portion disappears onto the tapered surface 22b and opens at the bottom surface 21c. And further, a circular, cylindrical groove 21e is formed in the direction of the outer wall's circumference of the cylindrical portion, and a C-shaped holding ring 23 made by removing a part of its circle is loosely inserted into the circular circumference groove 21e.

FIG. 5 is a perspective view showing a method for using the above-mentioned hose-inserting tool. In FIG. 5, the reference numeral 10 represents only a portion of the hole 10c for accommodating the water-supplying hose 6 of the electricity-supplying and water-supplying cord shown in FIG. 2. The water-supplying hose 6 is inserted from the insertion hole 22a of the hose guide 22 formed in the tool assembly 20 so as to pass through the opening 21b at the side of the groove 21a, and a support ring 23 is rotated in the direction shown by an arrow Y—Y in FIG. 3c in order to tightly enclose the groove 21a such that the tip end portion of the water-supplying hose 6 is located at the opening 21b.

Afterwards, the tool assembly 20 is inserted into the hole 10c of the water-supplying cord 10 through the rift 11 thereof as shown in FIG. 5, after opening the rift 11 by hand. And then, the water-supplying hose 6 and the water-supplying cord 10 are supported so as not to move, and the tool in itself 20 is moved along the rift 11 in the direction shown by an arrow L in FIG. 5. The water-supplying hose 6 is inserted in the hose guide 22, and the rift 11 is tightly closed by the elasticity of the water-supplying cord 10 while the hose 6 is inserted into the hole 10c through the rift 11 thereof.

Concerning the embodiment described heretofore, the tool in itself 20 is made of resin for the purpose of protecting the interior of the hole 10c from being injured when it is being used and the abrasion-proof quality of the hose guide 22 is improved as mentioned before. However, those matters are not always a necessary condition i.e. the tool itself 20 may be made of a uniform material and the hose guide 22 may be omitted while only the hose guide hole 24 remains.

As is apparent from the foregoing description, the work of inserting and accommodating the water-supplying hose 6 into the electricity-supplying and water-supplying cord 10 may be simplified and made more effective by the use of a hose-inserting tool 20 according to the present invention, and further it may be possible to exchange the water-supplying hose 6 for a new one or to clean the old one.

I claim:

1. A hose insertion tool adapted to be used for inserting an elongated element within a passageway of a tube having a resiliently closed rift leading to said passageway, said hose insertion tool comprising: an elongated tool body having a longitudinal axis, said body having one longitudinal end with a passage which opens up onto said one longitudinal end and which extends longitudinally into said body, said body having an outer wall extending longitudinally from said one longitudinal end, a groove in said body between one side of said outer wall and said passage, a guide channel in said body between an opposite side of said outer wall and said passage, said guide channel having a channel axis extending at an acute angle relative to said longitudinal axis, said one longitudinal end of said body being insertable in said rift by temporarily separating said rift and moving said tool body along said rift while simultaneously feeding said elongated element through said guide channel into said passageway of said tube.

2. A hose connection tool according to claim 1, wherein said tool body has an opposite longitudinal end opposite said one longitudinal end, said groove having one end portion extending from said one longitudinal end of said tool body, said groove having an opposite end portion which is tapered with a progressively decreasing width as said opposite longitudinal end of said tool body is approached.

3. A hose connection tool according to claim 1 further comprising a ring means disposed about said outer wall of said tool body.

4. A hose connection tool according to claim 3, wherein said ring means has a generally C-shaped configuration having a gap, said gap being disposed opposite said groove.

5. A hose connection tool according to claim 3, wherein said outer wall of said body has an indentation, said ring means being disposed in said indentation.

* * * * *